United States Patent [19]

Hausselt et al.

[11] 4,369,068

[45] Jan. 18, 1983

[54] GOLD CONTAINING PREPARATION FOR COATING METALLIC PARTS

[75] Inventors: Jürgen Hausselt, Langenselbold; Harry Schiwiora, Ispringen; Manfred Stümke, Pforzheim, all of Fed. Rep. of Germany

[73] Assignee: Degussa Aktiengesellschaft, Frankfurt, Fed. Rep. of Germany

[21] Appl. No.: 291,507

[22] Filed: Aug. 10, 1981

[51] Int. Cl.³ ............................ C09D 5/38; A61K 6/08
[52] U.S. Cl. ................................... 106/1.18; 106/1.13; 106/1.15; 106/35; 252/514; 260/998.11; 523/115; 433/200; 433/206
[58] Field of Search ................. 106/1.13, 1.15, 1.18, 106/193 M, 35; 252/514; 433/200, 206; 523/115

[56] References Cited

U.S. PATENT DOCUMENTS 3,450,545  6/1969  Ballard ........................... 106/1.13
3,872,360  3/1975  Sheard ........................... 106/1.18

Primary Examiner—Lorenzo B. Hayes
Attorney, Agent, or Firm—Cushman, Darby & Cushman

[57] ABSTRACT

Gold-containing preparations which improve the adhesiveness, guarantee an esthetic appearance, and should make possible a saving in gold consumption are needed for the production of intermediate layers for the facings of fired on alloys in the dental art with ceramic compositions. This is accomplished with preparation that contain 50 to 94% gold powder having a particle size <30μ, 5–40% binder made of organic solvent and resin components are 1–20% of a metal powder whose particle size is greater than of the gold powder used and whose melting temperature is above that of gold.

18 Claims, No Drawings

GOLD CONTAINING PREPARATION FOR COATING METALLIC PARTS

BACKGROUND OF THE INVENTION

The invention is directed to a gold-containing preparation for coating metallic particles, particularly for coating fired on alloys in the dental art before the facing with ceramic compositions, said preparation consisting of gold powder, an adhesive and a binder of one or more organic solvents and one or more resin components which binder is liquid at room temperature and volatilized or burned at firing temperature.

For many years in the dental art there has been known the facing of crowns and bridges made of fired on alloys with ceramic compositions. Thereby chiefly for esthetic reasons the metallic crown or bridge framework is entirely or partially coated with one or more tooth-colored ceramic layers. Likewise primarily for esthetic reasons gold-rich intermediate layers are used which bestow a warmer colored background to the slightly transparent dental porcelain than is possible to be done by the mostly metallic white customary fired on alloys.

The previously known gold-containing intermediate layer preparations lead to very smooth surfaces and practically cannot be influenced by the dental technician.

The previously known gold preparations are either melted or sintered on and contain gold powder or ball shaped gold particles (German AS No. 2851429), which lead to a uniform layer thickness and a very smooth surface.

On the other hand there has also long been known the significance of a sufficient dovetailing between the metallic fired on alloys and the dental ceramic for a good union. The proportions of the so-called physical union depends directly very strongly on the size, the shape and the roughness of the surface to be joined with the ceramic.

It is known from German OS No. 2525274 to use gold-containing preparations which besides gold powder and a flux also contains porcelain and zirconium oxide powder of very small particle size. However, this preparation leads to an unesthetic gray-white layer in the burning on the fired on alloy.

Therefore it was the problem of the present invention to find gold containing preparations for the coating of metallic portions, particularly for the coatings of fired on alloys in the dental art before the facing with ceramic compositions consisting of gold powder, an adhesive agent and a binder which is liquid at room temperature and is volatilized or burned at firing temperature, which after the firing guarantees the strongest possible dovetailing with the dental ceramic, has an esthetic appearance and makes possible a savings in the use of gold.

SUMMARY OF THE INVENTION

This problem was solved according to the invention by a gold-containing preparation made of 50 to 94 weight % gold powder having a particle size below 30μ, 5–40 weight % of a binder and 1 to 20 weight % of a metal powder as adhesive agent whose particle size is greater than that of the gold powder used and whose melting temperature is above that of gold. For example, the average particle size of the metal powder can be at least 10μ greater than the average particle size of the gold powder as is shown in the working examples.

Preferably these preparation contain 65 to 80 weight % gold powder, 15 to 25 weight % of binder and 5 to 10 weight % of metal powder. Advantageously the particle size of the gold powder is less than 10μ. The binder consists of one or more organic solvents, preferably 60 to 90 weight % and especially 65 to 85 weight % and one or more resin components, preferably 10 to 40 weight % and especially 15 to 35 weight %. As resin components above all, there can be used acrylate resins. e.g. polymethyl acrylate, polyethyl acrylate, or polybutyl acrylate, methacrylate resins, e.g. polymethyl methacrylate or polybutyl methacrylate, nitrocellulose, ethyl cellulose and natural or synthetic rubber, e.g. polyisobutylene butadiene-styrene copolymer, polybutadiene or polyisoprene. As solvents there can be used glycols, e.g. ethylene glycol, propylene glycol, diethylene glycol, or triethylene glycol, glycol ethers, e.g. the monomethyl ether of ethylene glycol, monomethyl ether of diethylene glycol, monoethyl ether of ethylene glycol, monoethyl ether of diethylene glycol, or the monobutyl ether of diethylene glycol, glycol esters, e.g. ethylene glycol monoacetate, terpene hydrocarbons, e.g. limonene, camphane, pinene and terpinene, terpene alcohols, e.g. terpineol and high boiling aliphatic hydrocarbons, e.g. decane.

As metal powders there have proven good palladium-, cobalt-, and/or nickel powder and/or powders of palladium-, gold-, cobalt-, and/or nickel alloys whereby their particle sizes are larger than that of the gold powder used and their melting or solidus temperature must be above the melting point of gold (1063° C.). It is advantageous if the alloying powder contains alloying elements which also are contained in the metallic parts to be coated. The pasty gold preparation of the invention can be readily applied to the metal parts to be coated, e.g. crowns or bridges with a brush or a felt. It has been proven that the surface roughness in addition to the gold is completely retained even after the firing on of the preparations if the firing on temperature is below the melting or solidus temperature of the metallic powder additive. There have proven good firing on temperatures between 600° and 1100° C. and firing on times between 0.5 and 10 minutes. The gold layers unite under these conditions with all current fired on alloys based on gold-platinum-palladium-silver, gold-silver, gold-palladium, nickel-chromium, cobalt-chromium and cobalt-palladium to an indissoluble union. The gold-containing preparations of the invention therewith are suited for all noble metal containing and noble metal free fired on alloys.

The thus produced intermediate layer causes a very good anchoring of the ceramic layer with the metallic crown or bridge part. All known dental ceramic compositions are suited for this. Bending tests on ceramic faced alloy sheets which were coated with an intermediate layer of a gold preparation of the invention show that with forceful separation of the ceramic layer from the metal the break takes place in the ceramic itself. A separation of the intermediate layer from the fired on alloy or from the ceramic could not be observed in any case.

Unless otherwise indicated all parts and percentages are by weight.

The compositions can comprise, consist essentially of, or consist of the stated materials.

Below there are set forth examples of several gold-containing preparations according to the invention.

DETAILED DESCRIPTION

EXAMPLE 1

75% gold powder, crystalline, particle size <10μ, 5% powder made of palladium with 20% gold and 5% tin, particle size <20μ, 15% butyl diethylene glycol acetate, 5% polymethyl methacrylate.

EXAMPLE 2

65% gold powder, crystalline, particle size <10, 10% powder made of gold with 10% platinum, 3% tin and 2% indium, particle size <37μ, 18% butyl diethylene glycol acetate, 7% ethyl cellulose.

EXAMPLE 3

70% gold powder, crystalline <10μ, 10% palladium powder, <37μ, 15% terpineol, 5% nitrocellulose.

EXAMPLE 4

40% gold powder, crystalline, <10μ, 35% gold powder, plate shaped, <10μ, 5% cobalt powder, <37μ, 16% high boiling aliphatic hydrocarbon, 4% polyisobutylene.

EXAMPLE 5

50% gold powder, crystalline, <10μ, 25% gold powder, plate shaped <10μ, 10% powder made of CoCr 27 Mo 5.5 Si 1, Mn 0.7, Fe 0.5, <37μ, 15% terpineol, 5% ethyl cellulose.

The entire disclosure of German application No. P 3027472.7 is hereby incorporated by reference.

What is claimed is:

1. A gold-containing preparation suitable for coating fired on alloys in the dental art before the facing with ceramic compositions, said preparation consisting essentially of gold powder, an adhesive and a binder of an organic solvent and a resin, said binder being liquid at room temperature and able to be volatilized or burned at the firing temperature, there being present 50 to 95 weight % gold powder having a particle size below 30μ, 5 to 40 weight % of the binder and 1 to 20 weight % of a metal powder as adhesive, the metal powder having an average particle size of 10 to 27 microns greater than and a melting temperature above that of the gold powder.

2. A gold-containing preparation according to claim 1 containing 65 to 80 weight % gold powder, 15 to 25 weight % binder and 5 to 10 weight % metal powder.

3. A gold-containing preparation according to claim 2 wherein the particle size of the gold powder is below 10μ.

4. A gold-containing preparation according to claim 1 wherein the particle size of the gold powder is below 10μ.

5. A gold-containing preparation according to claim 4 wherein the metal powder is palladium, cobalt, or nickel or an alloy of palladium, cobalt, nickel or gold or mixtures thereof.

6. A gold containing preparation according to claim 3 wherein the metal powder is palladium, cobalt, or nickel or an alloy of palladium, cobalt, nickel or gold or mixtures thereof.

7. A gold-containing preparation according to claim 2 wherein the metal powder is palladium, cobalt, or nickel or an alloy of palladium, cobalt, nickel or gold or mixtures thereof.

8. A gold-containing preparation according to claim 1 wherein the metal powder is palladium, cobalt, or nickel or an alloy of palladium, cobalt, nickel or gold or mixtures thereof.

9. A gold-containing preparation according to claim 8 wherein the metal powder includes at least one alloying element which is present in the metallic part to be coated.

10. A gold-containing preparation according to claim 9 wherein the metal powder includes at least one alloying element which is present in the metallic part to be coated.

11. A gold-containing preparation according to claim 8 wherein the metal powder includes at least one alloying element which is present in the metallic part to be coated.

12. A gold-containing preparation according to claim 7 wherein the metal powder includes at least one alloying element which is present in the metallic part to be coated.

13. A gold-containing preparation according to claim 6 wherein the metal powder includes at least one alloying element which is present in the metallic part to be coated.

14. A gold-containing preparation according to claim 5 wherein the metal powder includes at least one alloying element which is present in the metallic part to be coated.

15. A gold-containing preparation according to claim 8 including an alloying element present in the metallic part to be coated, said alloying element being a member of the group consisting of tin, indium, chromium, molybdenum, silicon, manganese, iron, and mixtures of at least two of said alloying elements.

16. A gold-containing preparation according to claim 8 wherein the binder contains 10 to 40 weight % resin and 60 to 90 weight % solvent.

17. A gold-containing preparation according to claim 7 wherein the binder contains 10 to 40 weight % resin and 60 to 90 weight % solvent.

18. A gold containing preparation according to claim 8 including an alloying element present in the metallic part to be coated, said alloying element being a metal selected from the group consisting of tin, indium, chromium, molybdenum, manganese, iron, and mixtures of at least two of said alloying elements.

* * * * *